US00RE45137E

(19) United States
(12) Reissued Patent
O'Hagan et al.

(10) Patent Number: US RE45,137 E
(45) Date of Reissued Patent: Sep. 16, 2014

(54) ADJUVANTED MENINGOCOCCUS COMPOSITIONS

(75) Inventors: Derek O'Hagan, East Hanover, NJ (US); Nicholas Valiante, East Hanover, NJ (US)

(73) Assignee: Novartis Vaccines and Diagnostics, Inc., East Hanover, NJ (US)

(21) Appl. No.: 13/587,840

(22) Filed: Aug. 16, 2012

Related U.S. Patent Documents

Reissue of:
(64) Patent No.: 7,838,015
Issued: Nov. 23, 2010
Appl. No.: 10/264,802
Filed: Oct. 3, 2002

U.S. Applications:
(60) Provisional application No. 60/326,929, filed on Oct. 3, 2001, provisional application No. 60/373,547, filed on Apr. 17, 2002, provisional application No. 60/380,677, filed on May 13, 2002.

(51) Int. Cl.

| | |
|---|---|
| ***A61K 39/02*** | (2006.01) |
| ***A61K 39/00*** | (2006.01) |
| ***A61K 39/116*** | (2006.01) |
| ***A61K 39/095*** | (2006.01) |
| ***A61K 38/00*** | (2006.01) |
| ***C07K 14/00*** | (2006.01) |

(52) U.S. Cl.
USPC ..... 424/250.1; 424/203.1; 424/234.1; 424/249.1; 424/184.1; 514/1.1; 530/350; 530/300; 530/825

(58) Field of Classification Search
None
See application file for complete search history.

(56) References Cited

U.S. PATENT DOCUMENTS 6,884,435 B1 * 4/2005 O'Hagan et al. ..... 424/489

FOREIGN PATENT DOCUMENTS

| | | | |
|---|---|---|---|
| WO | WO 99/36544 | * | 7/1999 |
| WO | WO 99/57280 | * | 11/1999 |
| WO | WO 00/06123 | * | 2/2000 |
| WO | WO 00/50075 | * | 8/2000 |
| WO | 01/64920 A2 | | 9/2001 |
| WO | 01/64922 A2 | | 9/2001 |
| WO | 03/020756 A2 | | 3/2003 |

OTHER PUBLICATIONS

Cruse et al. Illustrated Dictionary of Immunology. 2nd Edition, CRC Press, p. 46, 2003.*
Colman PM. Research Immunol. 145: 33-36, 1994.*
McGuinnes et al. Mol. Microbiol. 7: 505-514, 1993.*
McGuinnes et al. Lancet 337: 514-517, 1991.*
Singh M, et al: "Cationic Microparticles are an effective delivery system for immunie stimulatory CpG DNA" Pharmaceutical Research, New York, NY, US, vol. 18, No. 10, Oct. 2001, pp. 1476-1479, XP002976979 Issn: 0724-8741 * whole document*.*
O'Hagan D T et al: "poly(lactide-co-glycolide) Microparticles for the development of single-dose controlled-release vaccines" Advanced drug delivery reviews, Amsterdam, NL., vol. 32, 1998, pp. 225-246, XP000944990 Issn: 0169-409X * abstract *.*
Singh M, et al: "Advances in Vaccine Adjuvants" Nature Biotechnology, Nature Publishing Group, New York, NY, US, vol. 17, No. 11, Nov. 1999, pp. 1075-1081, XP000941305 Issn: 1087-0156 * the whole document *.*
A. Spickler et al., "Adjuvants in Veterinary Vaccines: Modes of Action and Adverse Effects", J Vet Intern Med 2003; 17:273-281.
J. Cox et al., "Adjuvants—A Classification and Review of Their Modes of Action", Vaccine, vol. 15, No. 3, pp. 248-256, 1997.
N. Burdin et al., "Immunological Foundations to the Quest for New Vaccine Adjuvants", Biodrugs 2004; 18 (2):79-93.

* cited by examiner

*Primary Examiner* — S. Devi
(74) *Attorney, Agent, or Firm* — Morrison & Foerster LLP

(57) ABSTRACT

A combination of CpG oligonucleotides and polymer microparticles is an extremely effective adjuvant for Neisserial antigens. The invention therefore provides a composition comprising: (a) a Neisserial antigen; (b) a CpG oligonucleotide; and (c) a biodegradable polymer microparticle.

46 Claims, No Drawings

ADJUVANTED MENINGOCOCCUS COMPOSITIONS

Matter enclosed in heavy brackets [ ] appears in the original patent but forms no part of this reissue specification; matter printed in italics indicates the additions made by reissue.

CROSS-REFERENCE TO RELATED APPLICATIONS

This application claims priority under 35 U.S.C §119(e)(1) to U.S. Provisional Applications Ser. Nos. 60/326,929 filed Oct. 3, 2001, 60/373,547, filed Apr. 17, 2002, 60/380,677, filed May 13, 2002, U.S. patent application Ser. No. 10/254,438 entitled Adjuvant Compositions filed, Sep. 24, 2002, now abandoned, and. U.S. patent application Ser. No. 10/265,083 entitled Adjuvant Compositions, filed Oct. 3, 2002, now U.S. Pat. No. 7,550,145. This application also claims priority to PCT Application No. PCT/US02/10869, filed Apr. 5, 2002, PCT Application No. PCT/US02/30423 entitled Adjuvant Compositions, filed Sep. 24, 2002, and PCT Application No. PCT/US02/31486 entitled Adjuvant Compositions, filed Oct. 3, 2002. All documents cited herein are incorporated by reference in their entirety.

*SUBMISSION OF SEQUENCE LISTING ON ASCII TEXT FILE*

*The content of the following submission on ASCII text file is incorporated herein by reference in its entirety: a computer readable form (CRF) of the Sequence Listing (file name: 223002126030SEQLIST.txt, date recorded: Aug. 16, 2012, size: 5 KB).*

TECHNICAL FIELD

The invention relates to vaccines, more particularly those against Neisseria meningitidis.

BACKGROUND ART

Genome sequences for Neisseria meningitidis (meningococcus) serogroups A [1] and B [2,3] have been reported. The serogroup B sequence has been studied to identify vaccine antigens [e.g. refs. 4 to 9] and candidate antigens have been manipulated to improve heterologous expression [refs. 10 to 12].

Antigens generally require the co-administration of adjuvants in order to enhance their immunogenicity in vaccines [13]. Freund's adjuvant has been used for serogroup B meningococcus [9], and the licensed vaccine Menjugate™ against serogroup C uses aluminium hydroxide [14]. Enhancement of the bactericidal activity of Neisseria antigens has also been reported by using oligonucleotide adjuvants containing CpG motifs [15].

It is an object of the invention to provide further and improved adjuvants for Neisserial antigens.

DISCLOSURE OF THE INVENTION

It has been found that a combination of CpG oligonucleotides and polymer microparticles is an extremely effective adjuvant for Neisserial antigens, with the combination giving much better results than either of the individual components. The invention therefore provides a composition comprising:

(a) a Neisserial antigen; (b) a CpG oligonucleotide; and (c) a biodegradable polymer microparticle.

The Neisserial Antigen

The Neisserial antigen may be a protein antigen, nucleic acid encoding a protein antigen, or a saccharide antigen. The antigen preferably elicits a bactericidal or protective immune response (e g antibody response) in a recipient mammal.

The antigen may be derived from any species of Neisseria including N. gonorrhoeae, N lactamica and N. meningitidis. It is preferably a N. meningitidis antigen and may be from any serogroup. Where the antigen is from serogroup B, it is preferred to use a protein antigen; where it is from serogroup A, C, W135 or Y then it is preferred to use a saccharide antigen. Where saccharide antigens are used, these will typically be derived from the bacterial capsular polysaccharide (e.g. oligosaccharides, such as those obtained by hydrolysis), and they will typically be conjugated to carrier proteins (e.g. to $CRM_{197}$).

Preferred protein antigens derived from serogroup B N. meningitidis are:

- a protein disclosed in any one of references 4, 5, 6, 7, 8 or 9 (in particular the 446 even SEQ IDs (i.e. 2, 4, 6, . . . , 890, 892) disclosed in reference 4, the 45 even SEQ IDs (i.e. 2, 4, 6, . . . , 88, 90) disclosed in reference 5 and the 1674 even SEQ IDs 2-3020, even SEQ IDs 3040-3114, and all SEQ IDs 3115-3241, disclosed in reference 6);
- a protein comprising an immunogenic fragment of one or more of the proteins disclosed in any one of references 4, 5, 6, 7, 8 or 9.
- a protein comprising a sequence having sequence identity (preferably greater than 50% e.g. 60%, 70%, 80%, 90%, 95%, 99% or more) to one or more of the proteins disclosed in any one of references 4, 5, 6, 7, 8 or 9.
- a protein disclosed in any one of references 10, 11 or 12.
- a protein comprising a sequence having sequence identity (preferably greater than 50% e.g. 60%, 70%, 80%, 90%, 95%, 99% or more) to one or more of the proteins disclosed in any one of references 10, 11 or 12.

A particularly preferred protein antigen from serogroup B N. meningitidis is protein '287'. This protein may be used in a wild-type form [e.g. GenBank accession gi:7228690, i.e., MFKRSVIAMACIFALSACGGGGGGSPD-VKSADTLSKPAAPVVSEKETEAKEDAPQAGSQ GQGAPSAQGGQDMAAVSEENTGNG-GAAATDKPKNEDEGAQNDMPQNAADTDSLTPN HTPASNMPAGNMENQAPDAGESEQPAN-QPDMANTADGMQGDDPSAGGENAGNTAAQ GTNQAENNQTAGSQNPASSTNPSATNSG-GDFGRTNVGNSVVIDGPSQNITLTHCKGDSC SGNN-FLDEEVQLKSEFEKLSDAD-KISNYKKDGKNDGKNDKFVGLVADSVQMKGINQYII FYKPKPTSFARFRRSARSRRSLPAEM-PLIPVNQADTLIVDGEAVSLTGHSGNIFAPEGNYR YLTYGAEKLPGGSYALRVQGEPSKGEM-LAGTAVYNGEVLHFHTENGRPSPSRGRFAAK VDFG-SKSVDGIIDSGDGLHMGTQKFKAAID-GNGFKGTWTENGGGDVSGKFYGPAGEEV AGKYSYRPTDAEKGGFGVFAGKKEQD (SEQ ID NO 1); alignments of polymorphic forms of 287 are shown in FIGS. 5 & 15 of ref. 8] but derivatives of the wild-type protein may be used. For instance, proteins having 50% or more sequence identity (e.g. 60%, 70%, 80%, 90%, 95%, 99% or more) to gi:7228690 may be used. Proteins comprising truncation or deletion variants of the protein may be used, such as the N-terminal truncated forms disclosed in references 10 to 12 ('ΔG287' in particular, in which the N-terminus of the protein up to and including the six repeated glycine residues is deleted). Fusion proteins comprising such 287 sequences may be used. All of these forms of 287, and more particularly those which retain the immunogenicity of wild-type 287 proteins, fall within the meaning of '287' as used herein.

Another particularly preferred protein antigen from serogroup B N. meningitidis is protein '961', also known as 'NadA' [16]. This protein may be used in a wild-type form [e.g. GenBank accession gi:7227256; alleles of 961 are disclosed in ref. 17] but derivatives of the wild-type protein may be used. For instance, proteins having 50% or more sequence identity (e.g. 60%, 70%, 80%, 90%, 95%, 99% or more) to gi:7227256 may be used. Proteins comprising truncation or deletion variants of the protein may be used, such as those disclosed in references 10 to 12 ('961c' in particular, which lacks the C-terminal membrane anchor). Fusion proteins comprising such 961 sequences may be used. All of these forms of 961, and particularly those which retain the immunogenicity of wild-type 961 proteins, fall within the meaning of '961' or 'NadA' as used herein.

Other preferred protein antigens are protein '741' and protein 'ORF46.1', and proteins 'ORF1', 'ORF4', 'ORF25', 'ORF40', 'ORF83', 'NMB1343', '230', '233', '292', '594', '687', '736', '907', '919', '936', '953', and '983'. Other preferred protein antigens are the hybrid proteins disclosed in references 10 to 12, particularly those comprising one or more of: a 287 protein, a 953 protein, a 936 protein and/or a 741 protein.

Protein antigens may be derived from any strain of N. meningitidis. It is preferred to use antigens from strains 2996, MC58, 95N477 and 394/98.

As well as strain variants, single or multiple conservative amino acid substitutions may be made with altering the immunogenicity of antigens used according to the present invention.

In addition to or in place of protein antigens, nucleic acid encoding a protein antigen may be included within compositions of the invention. The nucleic acid will be expressed in vivo once administered to a mammalian recipient and the protein antigen will be produced: Such nucleic acid immunization is well known [e.g. refs. 18 to 23 etc.]. The nucleic acid will typically be a DNA plasmid.

A preferred saccharide antigen derived from serogroup C N. meningitidisis the oligosaccharide conjugate used in Menjugate™ [24, 25], which contains 12 to 22 monosaccharide units from the serogroup C capsular polysaccharide.

A preferred saccharide antigen derived from serogroup A is an oligosaccharide in which one or more of the hydroxyl groups on the constituent monosaccharide units has been replaced by a blocking group [26].

Further oligosaccharide antigens from serogroups A, W135 and Y are disclosed in reference 27.

The composition of the invention may comprise more than one Neisserial antigen. Where saccharides from both serogroups A and C of N. meningitidis are included, it is preferred that the ratio (w/w) of MenA saccharide:MenC saccharide is greater than 1 (e.g. 2:1, 3:1, 4:1, 5:1, 10:1 or higher).

The composition of the invention is preferably an immunogenic composition or vaccine. Such compositions comprise an immunologically effective amount of the antigen. By 'immunologically effective amount', it is meant that the administration to an individual of a composition of the invention comprising that amount of antigen (either in a single dose or as part of a series) is effective for raising a therapeutic or prophylactic immune response. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating physician's assessment of the medical situation, and other relevant factors. The amount may fall in a relatively broad range that can be determined through routine trials. Antigens will typically be present at a concentration of at least 1 μg/ml each.

Dosage treatment may be a single dose or a multiple dose schedule (e.g. including booster doses).

The CpG Oligonucleotide

CpG oligonucleotides are known for use as vaccine adjuvants [e.g. ref. 28] and they induce strong Thl immune responses. They are useful as parenteral and mucosal adjuvants [29].

The CpG oligonucleotide used according to the present invention is a nucleic acid which includes at least one CG dinucleotide i.e. a cytosine nucleotide followed by a guanosine nucleotide. The oligonucleotide may contain multiple CG dinucleotides.

A CG sequence in the oligonucleotide may be flanked by two purines at the 5' side and two pyrimidines at the 3' side i.e. RRCGYY.

Cytosine nucleotides in the CpG oligonucleotide may be methylated, but it is preferred that they should be unmethylated.

The cytosine and guanosine nucleotides are preferably deoxynucleotides and the nucleic acid is preferably DNA. In order to enhance nuclease resistance, the oligonucleotide may comprise a modified backbone, such as a phosphorothioate backbone. As an alternative to using DNA, it is possible to use PNA (peptide nucleic acid). In addition, the oligonucleotides can comprise substitutions of the sugar moieties and nitrogenous base moieties.

The oligonucleotide preferably comprises between about 6 and about 100 nucleotides, more preferably between about 8 and about 50 nucleotides, most preferably between about 10 and about 40 nucleotides.

Oligonucleotides comprising at least one CG dinucleotide can conveniently be prepared using conventional oligonucleotide synthesis.

Examples of CpG oligonucleotide adjuvants are found in references 30 to 55.

The Biodegralable Polymer Microparticle

Biodegradable polymer microparticles are known for use as vaccine adjuvants [e.g. ref. 56]. They are useful as parenteral and mucosal adjuvants.

As well as being biodegradable, the polymer used to make the microparticles will generally be sterilizable and non-toxic (biocompatible). Suitable biodegradable polymers are readily commercially available and include those derived from polyhydroxybutyric acid; polycaprolactone; polyorthoester; polyanhydride; poly(hydoxybutyrate); and a poly (α-hydroxy acid). Preferred polymers are formed from one or more poly(α-hydroxy acid) e.g. poly(L-lactide), poly(D,L-lactide), copolymers of D,L-lactide and glycolide (such as poly(D,L-lactide-co-glycolide), or a copolymer of D,L-lactide and caprolactone. Microparticles formed from poly(D, L-lactide-co-glycolide) ('PLG') are preferred.

These polymers are available in a variety of molecular weights, and the appropriate molecular weight for a given antigen can readily be determined. For poly(L-lactide), a suitable molecular weight will be on the order of about 2000 to 250,000. For PLG, suitable molecular weights will generally range from about 10,000 to about 200,000, preferably about 15,000 to about 150,000, and most preferably about 50,000 to about 100,000.

For PLG microparticles, a variety of lactide:glycolide ratios may be used and the ratio is largely a matter of choice, depending in part on the co-administered antigen and the rate of degradation desired. For example, a 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component. A suitable ratio of lactide:glycolide is easily determined based on the nature of the antigen and disorder in question. Moreover, mixtures of microparticles with varying lactide:glycolide ratios will find use in the formulations in order to achieve the desired release kinetics for a given antigen and to provide for both a primary and secondary immune response. Degradation rate of the microparticles of the present invention can also be controlled by such factors as polymer molecular weight and polymer crystallinity.

The term 'microparticle' as used herein, refers to a particle of about 100 nm to about 150 μm in diameter, more preferably about 200 nm to about 30 μm in diameter, and most preferably about 500 nm to about 10 μm in diameter. Preferably, the microparticle will be of a diameter that permits parenteral administration without occluding needles and capillaries. Microparticle size is readily determined by techniques well known in the art, such as photon correlation spectroscopy, laser diffractometry and/or scanning electron microscopy. The term 'microparticle' includes 'nanoparticles' [57] within its scope. Preferred microparticles are microspheres, although lamellar particles [58] may also be used.

Microparticles may be prepared using any of several methods well known in the art [e.g ref. 59]. For example, double emulsion/solvent evaporation techniques [e.g. refs. 60 & 61] can be used to form the microparticles. These techniques involve the formation of a primary emulsion consisting of droplets of polymer solution containing the antigen (if antigen is to be entrapped in the microparticle), which is subsequently mixed with a continuous aqueous phase containing a particle stabilizer/surfactant.

More particularly, a water-in-oil-in-water (w/o/w) solvent evaporation system can be used to form the microparticles, as described in references 62, 63 and 64. In this technique, the particular polymer is combined with an organic solvent, such as ethyl acetate, dimethylchloride (also called methylene chloride and dichloromethane), acetonitrile, acetone, chloroform, and the like. The polymer will be provided in about a 2-15% solution, in organic solvent. An approximately equal amount of an antigen solution (e.g. in water) is added and the polymer/antigen solution emulsified using e.g. a homogenizer. The emulsion is then combined with a larger volume of an aqueous solution of an emulsion stabilizer such as polyvinyl alcohol (PVA) or polyvinyl pyrrolidone. The emulsion stabilizer is typically provided in about a 2-15% solution, more typically about a 4-10% solution. The mixture is then homogenized to produce a stable w/o/w double emulsion. Organic solvents are then evaporated.

The formulation parameters can be manipulated to allow the preparation of small (<5 μm) and large (>30 μm) microparticles [e.g. 63, 65]. For example, reduced agitation results in larger microparticles, as does an increase in internal phase volume. Small particles are produced by low aqueous phase volumes with high concentrations of PVA.

Microparticles can also be formed using spray-drying and coacervation [e.g. refs. 66, 67 & 68]; air-suspension coating techniques, such as pan coating and Wurster coating [69, 70]; ionic gelation [71].

Prior to use of the microparticles, antigen content is generally determined so that an appropriate amount of the microparticles may be delivered to the subject in order to elicit an adequate immune response.

Antigen content of the microparticles can be determined according to methods known in the art, such as by disrupting the microparticles and extracting entrapped antigen. For example, microparticles can be dissolved in dimethylchloride and the protein extracted into distilled water [e.g. refs. 72, 73, 74]. Alternatively, microparticles can be dispersed in 0.1 M NaOH containing 5% (w/v) SDS. The sample is agitated, centrifuged and the supernatant assayed for antigen using an appropriate assay [75].

Antigen and/or CpG-oligonucleotides can be located within or on the microparticles. Entrapment will generally be achieved by having the antigen/oligonucleotide present during formation of the microparticles, whereas surface adsorption is achieved by adding antigen/oligonucleotide to preformed microparticles.

One method for adsorbing antigen/oligonucleotide onto prepared microparticles is as follows. Microparticles are rehydrated and dispersed to an essentially monomeric suspension of microparticles using dialyzable anionic or cationic detergents. Useful detergents include, but are not limited to, any of the various N-methylglucamides (known as MEGAs), such as heptanoyl-N-methylglucamide (MEGA-7), octanoyl-N-methylglucamide (MEGA-8), nonanoyl-N-methylglucamide (MEGA-9), and decanoyl-N-methyl-glucamide (MEGA-10); cholic acid; sodium cholate; deoxycholic acid; sodium deoxycholate; taurocholic acid; sodium taurocholate; taurodeoxycholic acid; sodium taurodeoxycholate; 3-[(3-cholamidopropyl)dimethylammonio]-1-propane-sulfonate (CHAPS); N-octylglucoside; 3-[(3-cholamidopropyl) dimethylammonio]-2-hydroxy-1-propane-sulfonate (CHAPSO); N-dodecyl-N,N-dimethyl-3-ammonio-1-propane-sulfonate (ZWITTERGENT 3-12); N,N-bis-(3-D-gluconeamidopropyl)-deoxycholamide (DEOXY-BIGCHAP); sucrose monolaurate; glycocholic acid/sodium glycocholate; laurosarcosine (sodium salt); glycodeoxycholic acid/sodium glycodeoxycholate; sodium dodceyl sulfate (SDS); and hexadecyltrimethylammonium bromide (CTAB); dodecyltrimethylammonium bromide; hexadecyltrimethyl-ammonium bromide; tetradecyltrimethylammonium bromide; benzyl dimethyidodecylammonium bromide; benzyl dimethylhexadecylammonium chloride; benzyl dimethyltetra-decylammonium bromide. The above detergents are commercially available. Various cationic lipids known in the art can also be used as detergents [76, 77].

The microparticle/detergent mixture is then physically ground e.g. using a ceramic mortar and pestle, until a smooth slurry is formed. An appropriate aqueous buffer, such as phosphate buffered saline (PBS) or Tris buffered saline, is then added and the resulting mixture sonicated or homogenized until the microparticles are fully suspended. The antigen/oligonucleotide is then added to the microparticle suspension and the system dialyzed to remove detergent. The polymer microparticles and detergent system are preferably chosen such that the antigen/oligonucleotide will adsorb to the microparticle surface while still maintaining activity. The resulting microparticles containing surface adsorbed antigen/oligonucleotide may be washed free of unbound antigen/oligonucleotide and stored as a suspension in an appropriate buffer formulation, or lyophilized with the appropriate excipients, as described further below.

The Antigen/CpG/Microparticle Combination

Various physical relationships are possible between the three basic components of the compositions of the invention.

These arise because the microparticles have an internal volume and a surface, either of which may be used to locate the CpG-oligonucleotide and/or the antigen.

Thus, the antigen may be entrapped within microparticles, it may be adsorbed to microparticles, or it may be in simple admixture with the microparticles without entrapment or adsorption. Adsorption is preferred.

Similarly, the CpG-oligonucleotide may be entrapped within microparticles, it may be adsorbed to microparticles, or it may be in simple admixture with the microparticles. Adsorption can be achieved using detergents such as CTAB.

The CpG-oligonucleotide and the antigen may both have the same physical relationship to the microparticles as each other, or they may be different. Likewise the CpG-oligonucleotide and the antigen may be adsorbed onto the same microparticle or the CpG-oligonucleotide and the antigen may be adsorbed onto different microparticles. All possible combinations are encompassed within the present invention:

| | CpG-oligonucleotide | | |
|---|---|---|---|
| | Entrapped | Adsorbed | Mixed |
| Antigen | | | |
| Entrapped | Yes | Yes | Yes |
| Adsorbed | Yes | Yes | Yes |
| Mixed | Yes | Yes | Yes |

Compositions of the invention may include mixtures of the above e.g. some microparticles within the composition have entrapped antigen and some have adsorbed antigen.

Pharmaceutical Compositions

For pharmaceutical use, compositions of the invention will generally comprise a pharmaceutically acceptable carrier. This gives a pharmaceutical composition of the invention.

A pharmaceutically acceptable carrier can be any substance that does not itself induce the production of antibodies harmful to the patient receiving the composition, and which can be administered without undue toxicity. Suitable carriers can be large, slowly-metabolised macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers can include liquids such as water, saline, glycerol and ethanol. Auxiliary substances, such as wetting or emulsifying agents, pH buffering substances, and the like, can also be present in such vehicles. Liposomes are suitable carriers. A thorough discussion of pharmaceutical carriers is available in ref. 78.

Compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops, as a spray, or as a powder [e.g. 79].

The pharmaceutical composition is preferably sterile. It is preferably pyrogen-free. It is preferably buffered e.g. at between pH 6 and pH 8, generally around pH 7.

The pharmaceutical composition may be lyophilised.

The invention also provides a delivery device containing a pharmaceutical composition of the invention. The device may be, for example, a syringe.

Medical Treatments and Uses

Compositions of the invention may be used therapeutically (i.e. to treat an existing Neisserial infection) or prophylactically (i.e. to prevent future Neisserial infection).

The invention provides a composition of the invention for use as a medicament.

The invention also provides a method for raising an antibody response in a mammal, comprising administering a pharmaceutical composition of the invention to the mammal. The antibody response is preferably an IgA or IgG response and it is preferably bactericidal.

The invention also provides a method for treating a mammal suffering from a Neisserial infection and/or disease, comprising administering to the patient a pharmaceutical composition of the invention.

The invention also provides a method for protecting a mammal against a Neisserial infection and/or disease, comprising administering to the mammal a pharmaceutical composition of the invention.

The invention also provides the use of (a) a Neisserial antigen, (b) a CpG oligonucleotide, and (c) a biodegradable polymer microparticle, in the manufacture of a medicament for preventing or treating disease and/or infection in an mammal.

The mammal is preferably a human. The human may be an adult or, preferably, a child.

Compositions of the invention are particularly useful for immunising children and teenagers.

The uses and methods of the invention are particularly useful for treating/protecting against infections of N. meningitidis. The uses and methods are particularly useful for preventing/treating diseases including bacterial meningitis.

Efficacy of therapeutic treatment can be tested by monitoring Neisserial infection after administration of the composition of the invention. Efficacy of prophylactic treatment can be tested by monitoring anti-Neisseria immune responses after administration of the composition.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, ocular, nasal, aural, or pulmonary administration. Injection or intranasal administration is preferred.

Dosage treatment can be a single dose schedule or a multiple dose schedule.

Further Components

Compositions of the invention may include adjuvants in addition to CpG-oligonucleotides and polymer microparticles. Preferred further adjuvants include, but are not limited to: (A) aluminium compounds (e.g. aluminium hydroxide, aluminium phosphate, aluminium hydroxyphosphate, oxyhydroxide, orthophosphate, sulphate etc. [e.g. see chapters 8 & 9 of ref. 13]), or mixtures of different aluminium compounds, with the compounds taking any suitable form (e.g. gel, crystalline, amorphous etc.), and with adsorption being preferred; (B) MF59 (5% Squalene, 0.5% Tween®80, and 0.5% Span ®85, formulated into submicron particles using a microfluidizer) [see Chapter 10 of 13; see also ref. 80]; (C) liposomes [see Chapters 13 and 14 of ref. 13]; (D) ISCOMs

[see Chapter 23 of ref. 13], which may be devoid of additional detergent [81]; (E) SAF, containing 10% Squalane, 0.4% Tween®80, 5% pluronic-block polymer L121, and thr-MDP, either microfluidized into a submicron emulsion or vortexed to generate a larger particle size emulsion [see Chapter 12 of ref. 13]; (F) Ribi™ adjuvant system (RAS), (Ribi Immunochem) containing 2% Squalene, 0.2% Tween®80, and one or more bacterial cell wall components from the group consisting of monophosphorylipid A (MPL), trehalose dimycolate (TDM), and cell wall skeleton (CWS), preferably MPL+CWS (Detox™); (G) saponin adjuvants, such as QuilA or QS21 [see Chapter 22 of ref. 13], also known as Stimulon™ [82]; (H) chitosan [e.g. 83]; (I) complete Freund's adjuvant (CFA) and incomplete Freund's adjuvant (IFA); (J) cytokines, such as interleukins (e.g. IL-1, IL-2, IL-4, IL-5, IL-6, IL-7, IL-12, etc.), interferons (e.g. interferon-γ), macrophage colony stimulating factor, tumor necrosis factor, etc. [see Chapters 27 & 28 of ref. 13]; (K) monophosphoryl lipid A (MPL) or 3-O-deacylated MPL (3dMPL) [e.g. chapter 21 of ref. 13]; (L) combinations of 3dMPL with, for example, QS21 and/or oil-in-water emulsions [84]; (M) a polyoxyethylene ether or a polyoxyethylene ester [85]; (N) a polyoxyethylene sorbitan ester surfactant in combination with an octoxynol [86] or a polyoxyethylene alkyl ether or ester surfactant in combination with at least one additional non-ionic surfactant such as an octoxynol [87]; (N) a particle of metal salt [88]; (O) a saponin and an oil-in-water emulsion [89]; (P) a saponin (e.g. QS21)+3dMPL+IL-12 (optionally+a sterol) [90]; (Q) E. coli heat-labile enterotoxin ("LT"), or detoxified mutants thereof, such as the K63 or R72 mutants [e.g. Chapter 5 of ref. 91]; (R) cholera toxin ("CT"), or detoxified mutants thereof [e.g. Chapter 5 of ref. 91]; (S) double-stranded RNA and (T) other substances that act as immunostimulating agents to enhance the effectiveness of the composition [e.g. see Chapter 7 of ref. 13]. Alum (especially aluminium phosphate and/or hydroxide) and MF59 are preferred further adjuvants for parenteral immunisation. Mutant toxins are preferred mucosal adjuvants.

Muramyl peptides include N-acetyl-muramyl-L-threonyl-D-isoglutamine (thr-MDP), N-acetyl-normuramyl -L-alanyl-D-isoglutamine (nor-MDP), N-acetylmuramyl-L-alanyl-D-isogl utaminyl-L-alanine-2-(1'-2'-dipal mitoyl-sn-glycero-3-hydroxyphosphoryloxy)-ethylamine MTP-PE), etc.

As well as Neisserial antigen(s), the composition may comprise further antigenic components. Antigens which can be included in the composition of the invention include:

- antigens from Helicobacter pylori such as CagA [92 to 95], VacA [96, 97], NAP [98, 99, 100], HopX [e.g. 101], HopY [e.g. 101] and/or urease.
- an outer-membrane vesicle (OMV) preparation from N. meningitidisserogroup B, such as those disclosed in refs. 102, 103, 104, 105 etc.
- a saccharide antigen from Streptococcus pneumoniae [e.g. 106, 107, 108].
- an antigen from hepatitis A virus, such as inactivated virus [e.g. 109, 110].
- an antigen from hepatitis B virus, such as the surface and/or core antigens [e.g. 110, 11].
- an antigen from hepatitis C virus [e.g. 112].
- an antigen from Bordetella pertussis, such as pertussis holotoxin (PT) and filamentous haemagglutinin (FHA) from B. pertussis, optionally also in combination with pertactin and/or agglutinogens 2 and 3 [e.g. refs. 113 & 114].
- a diphtheria antigen, such as a diphtheria toxoid [e.g. chapter 3 of ref. 115] e.g. the $CRM_{197}$ mutant [e.g 116].
- a tetanus antigen, such as a tetanus toxoid [e.g. chapter 4 of ref. 115].
- a saccharide antigen from Haemophilus influenzae B [e.g. 23].
- an antigen from Chlamydia pneumoniae [e.g 117, 118, 119, 120, 121, 122, 123].
- an antigen from Chlamydia trachomatis [e.g. 124].
- an antigen from Porphyromonas gingivalis [e.g. 125].
- polio antigen(s) [e.g. 126, 127] such as IPV or OPV.
- rabies antigen(s) [e.g. 128] such as lyophilised inactivated virus [e.g. 129, RabAvert™].
- measles, mumps and/or rubella antigens [e.g chapters 9, 10 & 11 of ref. 115].
- antigen(s) from influenza virus [e.g. chapter 19 of ref. 115], such as the haemagglutinin and/or neuraminidase surface proteins
- antigen(s) from a paarmyxovirus such as respiratory syncytial virus (RSV [130, 131]) and/or parainfluenza virus (PIV3 [132]).
- an antigen from Moraxella catarrhalis [e.g. 133].
- an antigen from Streptococcus agalactiae (group B streptococcus) [e.g. 134, 135].
- an antigen from Streptococcus pyogenes (group A streptococcus) [e.g. 135, 136, 137].
- an antigen from Staphylococcus aureus [e.g. 138].
- an antigen from Bacillus anthracis [e.g. 139, 140, 141].
- an antigen from a virus in the flaviviridae family (genus flavivirus), such as from yellow fever virus, Japanese encephalitis virus, four serotypes of Dengue viruses, tick-borne encephalitis virus, West Nile virus.
- a pestivirus antigen, such as from classical porcine fever virus, bovine viral diarrhoea virus, and/or border disease virus.
- a parvovirus antigen e.g. from parvovirus B19.
- a prion protein (e.g the CJD prion protein)
- an amyloid protein, such as a beta peptide [142]
- a cancer antigen, such as those listed in Table 1 of ref. 143 or in tables 3 & 4 of ref. 144.

The composition may comprise one or more of these further antigens.

Toxic protein antigens may be detoxified where necessary (e.g. detoxification of pertussis toxin by chemical and/or genetic means [114]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens are preferably adsorbed to an aluminium salt.

Antigens in the composition will typically be present at a concentration of at least 1 μg/ml each.

In general, the concentration of any given antigen will be sufficient to elicit an immune response against that antigen.

As an alternative to using proteins antigens in the composition of the invention, nucleic acid encoding the antigen may be used. Protein components of the compositions of the invention may thus be replaced by nucleic acid (preferably DNA e.g. in the form of a plasmid) that encodes the protein.

Definitions

The term "comprising" means "including" as well as "consisting" e.g. a composition "comprising" X may consist exclusively of X or may include something additional e.g. X+Y.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 145. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is taught in reference 146.

MODES FOR CARRYING OUT THE INVENTION

Parenteral Prime & Mucosal Boost with Neisseria meningitidis Serogroup B Antigen Reference 6 discloses a protein from serogroup B N. meningitidis called '287'. References 10 to 12 disclose ways of improving its expression. One way involves deleting the N-terminus of the protein up to and including the six repeated glycine residues. This protein is referred to as 'ΔG287'.

Mice were primed and boosted with MenB ΔG287 antigen (20 μg/dose) from strain 2996, formulated for intramuscular (IM) administration by adsorption to PLG microparticles, with or without CpG oligonucleotide (also adsorbed to the microparticles). An additional formulation for intranasal (IN) administration used LT-K63 adjuvant. Mice received either 3 IM doses or 2 IM then 2 IN doses (doses at: day 0; day 28; day 84; and, optionally, day 98).

| | | | | Antibody GMT 2 weeks after | | |
|---|---|---|---|---|---|---|
| Group | Formulation | Route | Dose | dose 2 | Dose 3 | dose 4 |
| 1 | PLG/287 | IM | 1, 2, 3 | 10,729 | 2,853 | — |
| 2 | PLG/287 + PLG/CpG | IM | 1, 2, 3 | 15,673 | 4,163 | — |
| 3 | PLG/287 | IM | 1, 2 | 9,064 | 7,948 | 9,412 |
| | 287 + LT-K63 | IN | 3, 4 | | | |
| 4 | PLG/287 + PLG/CpG | IM | 1, 2 | 34,891 | 15,167 | 16,556 |
| | 287 + LT-K63 | IN | 3, 4 | | | |

Thus, the inclusion of CpG-oligonucleotide enhanced antibody titers against intramuscularly administered MenB protein 287 (compare groups 1 & 2). Titers could be enhanced by replacing a third intramuscular dose with two intranasal doses (compare groups 1 & 3). The CpG enhancement was also seen in the intramuscular/intranasal regime (compare groups 3 & 4).

Comparison of Adjuvants for MenB Protein 287

ΔG287 was formulated with various adjuvants and administered to mice. Sera from the mice were assessed using the bactericidal antibody (BCA) assay and titers were as follows:

| Adjuvant | BCA post-2 | BCA post-3 |
|---|---|---|
| Freund's adjuvant | 2048 | 8192 |
| Alum | <4 | 256 |
| Alum + CpG oligonucleotide | 256 | 4096 |
| MF59 | <4 | <4 |
| CpG oligonucleotide | <4 | 128 |
| PLG microparticles (adsorbed) | 8 | 1024 |
| PLG microparticles (adsorbed) + CpG | 2048 | 16384 |

CpG-oligonucleotide was thus only mildly effective as an adjuvant, almost comparable to alum. The PLG microparticles were more effective than both alum and CpG, but not as effective as Freund's adjuvant. In marked contrast, however, the mixture of CpG and PLG matched the adjuvanticity of Freund's adjuvant at the post-second immunization stage and exceeded Freund's adjuvant post-third immunization.

Enhancement of PLG adjuvanticity by using CpG was also seen in a separate study (02-0279):

| Adjuvant | GMT post-2 | GMT post-3 |
|---|---|---|
| MF59 | 6967 | 13417 |
| PLG microparticles (adsorbed) | 7070 | 11367 |
| PLG microparticles (adsorbed) + CpG | 15099 | 26833 |

Effect of Adsorption on Adjuvanticity

The effect of adsorption on adjuvanticity was studied. Protein ΔG287 was either adsorbed onto PLG microparticles using DSS surfactant or SDS or was simply mixed with the particles. Immunisations were performed on days 0, 21 and 35 and titers were assessed on days 35 and 49. Results were as follows:

| | | Antibody titer 2 weeks after | |
|---|---|---|---|
| Formulation | BCA | dose 2 | Dose 3 |
| CpG + 287 adsorbed on PLG (DSS) | 4096 | 45817 | 67921 |
| CpG + 287 adsorbed on PLG (SDS) | 4096 | 39730 | 29911 |
| CpG + 287 + PLG (no adsorption) | <16 | 62 | 1065 |
| DSS + 287 adsorbed on alum | <16 | 1209 | 1249 |
| CpG + 287 adsorbed on Alum | 1024 | 4054 | 12236 |
| 287 adsorbed on alum | 128 | 646 | 2454 |

The adjuvanticity of CpG and microparticle mixtures for ΔG287 is thus optimal when the antigen is adsorbed to microparticles.

Reference 6 discloses a protein from serogroup B N. meningitidis called '961' (now known as 'NadA' [16,17]). References 10 to 12 disclose ways of improving the expression of NadA. One way involves deleting the C-terminus of the protein to remove its membrane anchor (i.e. remove amino acids 351-405 for strain 2996), as well as natural removal of its leader peptide. This protein is referred to as '961 c'. The effect of adsorption on PLG adjuvanticity when co-administered with CpG was studied for 961c, as described above for 287:

| Formulation | BCA | Antibody titer 2 weeks after dose 3 |
|---|---|---|
| 961 adsorbed on PLG (SDS) | 2048 | 20661 |
| 961 + PLG (no adsorption) | 256 | 1706 |
| 287 adsorbed on PLG | 4096 | 63057 |
| 287 adsorbed on PLG + 961 soluble | 4096 | 287: 86052; 961: 1924 |
| 287 adsorbed on PLG + 961 adsorbed on PLG | 8192 | 287: 107142; 961: 11717 |
| 287 (not adsorbed) + 961 (not adsorbed) + 'blank' PLG | 1024 | 287: 1266; 961: 145 |
| 287 (adsorbed) + 961 (adsorbed) + 'blank' PLG | 8192 | 287: 78176; 961: 20876 |

As for ΔG287, therefore, the adjuvanticity of CpG and microparticle mixtures for 961c is optimal when the antigen is adsorbed to microparticles. This is true for the antigen on its own and the antigen when combined with ΔG287.

For both ΔG287 and 961c, therefore, singly and combined, the best adjuvanticity for CpG and PLG mixtures is seen when the antigens are adsorbed onto the PLG microparticles.

PLG, CpG, alum and MF59

Various combinations of PLG, CpG and alum were tested for protein ΔG287, expressed as a His-tagged product. Serum bactericidal titers after three immunisations were as follows:

| Adjuvant | Titer |
|---|---|
| Alum | 2048 |
| Alum + CpG | 32768 |
| MF59 | 8192 |
| MF59 + CpG | 32768 |
| PLG (antigen adsorbed to PLG) | 1024 |
| PLG + CpG (antigen and CpG both adsorbed to PLG) | 4096 |
| PLG + MF59 (antigen adsorbed to PLG) | 2048 |
| PLG + MF59 + CpG (antigen adsorbed to PLG) | 8192 |
| Complete Freund's | 32768 |
| PLG + Complete Freund's (antigen adsorbed to PLG) | 2048 |

Similar experiments were performed and results were as follows:

| Adjuvant | Titer |
|---|---|
| PLG (antigen adsorbed to PLG) | 1024 |
| PLG + CpG (antigen adsorbed to PLG) | 16384 |
| PLG + CpG (antigen and CpG both adsorbed to PLG) | 16384 |
| PLG + alum (antigen adsorbed to PLG) | 1024 |
| PLG + alum + CpG (antigen adsorbed to PLG) | 16384 |
| PLG + alum + CpG (antigen and CpG both adsorbed to PLG) | 8192 |
| PLG + MF59 (antigen adsorbed to PLG) | 4096 |
| PLG + MF59 + CpG (antigen adsorbed to PLG) | 16384 |
| Alum (antigen adsorbed to alum) | 256 |
| CpG | 128 |
| Alum + CpG | 1024 |
| Alum + CpG + PLG (antigen adsorbed to alum; CpG adsorbed to PLG) | 4096 |
| CpG + PLG (CpG adsorbed on PLG; antigen not adsorbed) | 64 |

Thus, MF59 and alum can further enhance efficacy of CpG/PLG mixtures, adsorption of CpG to PLG microparticles is not necessary for adjuvanticity, but adsorption of antigen to microparticles is again seen to be optimal.

Antigen Mixtures

The effect of adsorption on adjuvanticity was studied for proteins ΔG287 and 961 c, singly and in combination. Antibody titers after three doses were as follows:

| | Antibody GMT against | |
|---|---|---|
| Formulation | 287 | 961 |
| CpG + 961 adsorbed on PLG | — | 20661 |
| CpG + 961 + PLG (no adsorption) | — | 1706 |
| CpG + 961 + 287 adsorbed on PLG | 86052 | 1924 |
| CpG + 961 adsorbed on PLG + 287 adsorbed on PLG | 107142 | 11717 |
| CpG + 287 adsorbed on PLG | 63057 | — |
| CpG + 287 & 961 co-adsorbed on PLG | 57306 | 6251 |
| CpG + 961 adsorbed on PLG + 287 adsorbed on PLG + PLG | 78176 | 20876 |
| 287 + 961 + PLG (no adsorption of antigens) | 1266 | 145 |

As for ΔG287, therefore, the adjuvanticity of CpG and microparticle mixtures for protein 961 c is optimal when the antigen is adsorbed to microparticles.

Further combinations of adjuvants with PLG microparticles were tested for proteins ΔG287 and 961c. The CpG was either soluble or was adsorbed to PLG microparticles. Results were as follows:

| | | GMT against | |
|---|---|---|---|
| Formulation + PLG microparticles | BCA | 287 | 961 |
| 287 (adsorbed on PLG) + 961 (adsorbed on PLG) | 256 | 5719 | 2412 |
| 287 (adsorbed on PLG) + 961 (adsorbed on PLG) + CpG | 512 | 17553 | 8627 |
| 287 (adsorbed on PLG) + 961 (adsorbed on PLG) + CpG (adsorbed on PLG) | 1024 | 16906 | 6720 |
| 287 (adsorbed on PLG) + 961 (adsorbed on PLG) + MF59 | 64 | 4636 | 3969 |
| 287 (adsorbed on PLG) + 961 (adsorbed on PLG) + MF59 + CpG | 2048 | 23642 | 48446 |

Similar work was performed on groups of 10 CD-1 mice, using 20 μg per PLG-adsorbed antigen per IM dose (days 0, 21 and 35). Where CpG was present, it was given at 10 μg per dose. ELISA titers (GMT) were calculated as the reciprocal serum dilution giving $OD_{450nm}$ 0.5, and sera were tested for both antigens. Serum bactericidal activity titers (SBA) are calculated as the reciprocal serum dilution killing 50% of target bacteria, and sera were tested for activity against 2996 strain and against MC58, a heterologous strain. Titers at day 49 (2 weeks post-third dose) were as follows:

| | | | GMT | | SBA | |
|---|---|---|---|---|---|---|
| 287 | 961 | Extra adjuvant | 287 | 961 | 2996 | MC58 |
| X | — | — | 8375 | — | 512 | <4 |
| X | — | Soluble CpG | 33736 | — | 1024 | 128 |
| X | — | PLG-adsorbed CpG | 32058 | — | 1024 | 64 |
| — | X | — | — | 3818 | nd | nd |
| — | X | Soluble CpG | — | 14149 | 2048 | <4 |
| — | X | PLG-adsorbed CpG | — | 18526 | 2048 | <4 |
| X | X | — | 13557 | 2476 | nd | nd |
| X | X | Soluble CpG | 21664 | 6557 | 8192 | 64 |
| X | X | PLG-adsorbed CpG | 27259 | 7510 | 2048 | 128 |
| X | X | Soluble CpG + MF59 | 27981 | 26826 | 2048 | 256 |
| Control: soluble 287 with CFA | | | 37889 | — | 1024 | <32 |
| Control: soluble 961 with CFA | | | — | 50453 | 4096 | <4 |
| Control: soluble 287 and 961 with CFA | | | 1678 | 27069 | 512 | <32 |

Reference 12 discloses a combination of three proteins which, between them, include five different N. meningitidis antigens: (1) $961c_{2996}$; (2) $\Delta G287_{NZ}$-$953_{2996}$; and (3) $936_{2996}$-$\Delta G741_{MC58}$. The antigen mixture was tested in reference 12 using aluminum hydroxide adjuvant. According to the present invention, the antigen mixture is adjuvanted by adsorption to a biodegradable polymer microparticle plus a CpG oligonucleotide. Titers after the third dose were as follows:

| | ELISA GMT | | | | SBA (against seven strains) | | | | | | |
|---|---|---|---|---|---|---|---|---|---|---|---|
| Immunisation | 961 | 287 | 741 | 953 | 2996 | MC58 | BZ133 | 394/98 | NGH38 | F6124 | 44/76 |
| (1) 961 on alum | 12346 | — | — | — | 4096 | <4 | <4 | <4 | <4 | 64 | <4 |
| (2) 287-953 on alum | — | 6415 | — | 585 | 1024 | 1024 | 256 | 1024 | 4096 | 256 | 1024 |
| (3) 936-741 on alum | — | — | 10625 | — | <4 | 32768 | 16384 | 1024 | 128 | 16384 | 32768 |
| (1), (2) & (3) on alum | 42302 | 18206 | 33881 | 4549 | 8192 | 32768 | 32768 | 2048 | 4096 | 32768 | 65536 |
| (1) 961 on PLG | 14185 | — | — | — | 2048 | 4 | <4 | <4 | 16 | 256 | <4 |
| (2) 287-953 on PLG | — | 43515 | — | 478 | 2048 | 128 | 2048 | 2048 | 8192 | 4096 | 128 |
| (3) 936-741 on PLG | — | — | 16150 | — | <4 | 32768 | 16384 | 1024 | 512 | 8192 | 262144 |
| (1), (2) & (3) on PLG | 6735 | 24304 | 13801 | 1214 | 4096 | 65536 | 32768 | 2048 | 4096 | 32768 | 65536 |
| (1), (2) & (3) on PLG + CpG | 10896 | 40697 | 26966 | 2301 | 8192 | 262144 | 65536 | 4096 | 8192 | 32768 | 262144 |

Compared to the aluminum adjuvant used in reference 12, the PLG+CpG mixture leads to lower overall antibody titers (except for protein 287) but, importantly, gives higher bactericidal titers against a wide range of strains. Although absolute titers are lower, therefore, the adjuvant of the invention therefore advantageously shifts antibody production towards bactericidal antibodies.

It will be understood that the invention has been described by way of example only and modifications may be made whilst remaining within the scope and spirit of the invention.

REFERENCES (The Contents of which are hereby Incorporated by Reference)

[1] Parkhill et al. (2000) Nature 404:502-506.
[2] Tettelin et al. (2000) Science 287:1809-1815.
[3] WO00/66791.
[4] WO99/24578.
[5] WO99/36544.
[6] WO99/57280.
[7] WO00/22430.
[8] WO00/66741.
[9] Pizza et al. (2000) Science 287:1816-1820.
[10] WO01/64920.
[11] WO01/64922.
[12] International patent application PCT/IB02/03904.
[13] Vaccine design the subunit and adjuvant approach, eds. Powell & Newman, Plenum Press 1995 (ISBN 0-306-44867-X).
[14] Jones (2001) Curr Opin Investig Drugs 2:47-49.
[15] WO00/50075.
[16] Comanducci et al. (2002)J. Exp. Med. 195:1445-1454.
[17] International patent application PCT/IB02/03396.
[18] Strugnell et al. (1997) Immunol Cell Biol 75(4):364-369.
[19] Robinson & Torres (1997) Seminars in Immunol 9:271-283.
[20] Donnelly et al. (1997) Annu Rev Immunol 15:617-648.
[21] DNA Vaccination—Genetic Vaccination (eds. Koprowski et al; 1998) ISBN 3540633928.
[22] Brunham et al. (2000) J. Infect Dis 181 Suppl 3:S538-43.
[23] Svanholm et al. (2000) Scand J Immunol 51(4):345-53.
[24] Costantino et al. (1992) Vaccine 10:691-698.
[25] Costantino et al. (1999) Vaccine 17:1251-1263.
[26] UK patent applications 0207117.3 & 0220195.2
[27] International patent application PCT/IB02/03191.
[28] McCluskie et al. (2001) Curr. Opin. Investig. Drugs 2:35-39.
[29] McCluskie et al. (2001) Crit. Rev. Immunol. 21:103-120.
[30] Krieg et al. (1998) Proc. Natl. Acad. Sci. USA, 95, 12631-12636,
[31] Klinman et al. (1996), Proc. Natl. Acad. Sci USA, 93, 2879-2883
[32] Weiner et al. (1997) Proc. Natl. Acad. Sci. USA, 94, 10833-10837
[33] Chu et al. (1997) J. Exp. Med., 186, 1623-1631
[34] Brazolot-Millan et al. (1998) Proc. Natl. Acad. Sci. USA, 95, 15553-15558
[35] Ballas et al (1996) J. Immunol., 157, 1840-1845
[36] Cowdery et al. (1996) J. Immunol., 156, 4570-4575
[37] Halpern et al. (1996) Cell. Immunol., 167, 72-78
[38] Yamamoto et al. (1988) Jpn J. Cancer Res., 79, 866-873
[39] Stacey et al. (1996) J. Immunol., 157, 2116-2122
[40] Messina et al. (1991) J. Immunol., 147, 1759-1764
[41] Yi et al. (1996) J. Immunol., 157, 4918-4925
[42] Yi et al (1996) J. Immunol., 157, 5394-5402
[43] Yi et al. (1998) J. Immunol., 160, 4755-4761
[44] Roman et al. (1997) Nat. Med, 3, 849-854
[45] Davis et al. (1998) J. Immunol., 160, 870-876
[46] Lipford et al (1997) Eur. J. Immunol., 27, 2340-2344
[47] Moldoveanu et al. (1988) Vaccine, 16, 1216-1224
[48] Yi et al. (1998) J. Immunol., 160, 5898-5906
[49] WO96/02555
[50] WO98/16247
[51] WO98/18810
[52] WO98/40100
[53] WO98/55495
[54] WO98/37919a
[55] WO98/52581
[56] Gupta et al. (1998) Adv Drug Deliv Rev 32:225-246.
[57] Ravi Kumar (2000) J. Pharm Pharm Sci 3:234-258.
[58] Jabbal-Gill et al. (2001) Adv Drug Deliv Rev 51:97-111.
[59] Jain (2000) Biomaterials 21:2475-2490.
[60] U.S. Pat. No. 3,523,907
[61] Ogawa et al. (1988) Chem. Pharm. Bull. 36:1095-1103.
[62] O'Hagan et al. (1993) Vaccine 11:965-969.
[63] Jeffery et al. (1993) Pharm. Res. 10:362-368.
[64] WO 00/06133
[65] McGee et al. (1997) J. Microencapsul. 14:197-210.
[66] Thomasin et al. (1996) J. Controlled Release 41:13ff
[67] U.S. Pat. No. 2,800,457
[68] Masters, K. (1976) Spray Drying 2nd Ed. Wiley, New York
[69] Hall et al., (1980) The "Wurster Process" in Controlled Release Technologies. Methods, Theory, and Applications (A. F. Kydonieus, ed.), Vol. 2, pp. 133-154 CRC Press, Boca Raton, Fla.
[70] Deasy, P. B. (1988) Crit. Rev Ther. Drug Carrier Syst. S(2):99-139
[71] Lim et al. (1980) Science 210:908-910.
[72] Cohen et al (1991) Pharm. Res. 8:713ff
[73] Eldridge et al. (1991) Infect. Immun. 59:2978ff
[74] Eldridge et al. (1990) J. Controlled Release 1:205ff
[75] O'Hagan et al. (1994) Int. J Pharm. 103:37-45.
[76] Balasubramaniam et al. (1996) Gene Ther 3:163-172.

[77] Gao & Huang (1995) Gene Ther. 2:7110-7122.
[78] Gennaro (2000) Remington' The Science and Practice of Pharmacy. 20th edition, ISBN: 0683306472.
[79] Almeida & Alpar (1996) J. Drug Targeting 3:455-467.
[80] WO90/14837.
[81] WO00/07621.
[82] WO00/62800.
[83] WO99/27960.
[84] European patent applications 0835318, 0735898 and 0761231.
[85] WO99/52549.
[86] WO01/21207.
[87] WO01/21152.
[88] WO00/23105.
[89] WO99/11241.
[90] WO98/57659.
[91] Del Giudice et al. (1998) Molecular Aspects of Medicine, vol. 19, number 1.
[92] Covacci & Rappuoli (2000) J. Exp. Med. 19:587-592.
[93] WO93/18150.
[94] Covacci et al. (1993) Proc. Natl. Acad. Sci. USA 90: 5791-5795.
[95] Tummuru et al (1994) Infect. Immun. 61:1799-1809.
[96] Marchetti et al. (1998) Vaccine 16:33-37.
[97] Telford et al. (1994) J. Exp. Med. 179:1653-1658.
[98] Evans et al (1995) Gene 153:123-127.
[99] WO96/01272 & WO96/01273, especially SEQ ID NO:6.
[100] WO97/25429.
[101] WO98/04702.
[102] WO01/52885.
[103] Bjune et al. (1991) Lancet 338(8775): 1093-1096.
[104] Fukasawaetal. (1999) Vaccine 17:2951-2958.
[105] Rosenqvistetal. (1998) Dev. Biol. Stand. 92:323-333.
[106] Watson (2000) Pediatr Infect Dis J. 19:331-332.
[107] Rubin (2000) Pediatr Clin North Am 47:269-285, v.
[108] Jedrzejas (2001) Microbiol Mol Biol Rev 65:187-207.
[109] Bell (2000) Pediatr Infect Dis J 19:1187-1188.
[110] Iwarson (1995) APMIS 103:321-326.
[111] Gerlich et al (1990) Vaccine 8 Suppl:S63-68 & 79-80.
[112] Hsu et al. (1999) Clin Liver Dis 3:901-915.
[113] Gustafsson et al. (1996) N. Engl. J. Med 334:349-355.
[114] Rappuoli et al. (1991) TIBTECH9:232-238.
[115] Vaccines (1988) eds. Plotkin & Mortimer. ISBN 0-7216-1946-0.
[116] Del Guidice et al. (1998) Molecular Aspects of Medicine 19:1-70.
[117] WO02/02606.
[118] Kalman et al. (1999) Nature Genetics 21:385-389.
[119] Read et al. (2000) Nucleic Acids Res 28:1397-406.
[120] Shirai et al. (2000) J. Infect. Dis. 181(Suppl 3):S524-S527.
[121] WO99/27105.
[122] WO00/27994.
[123] WO00/37494.
[124] WO99/28475.
[125] Ross et al (2001) Vaccine 19:4135-4142.
[126] Sutter et al. (2000) Pediatr Clin North Am 47:287-308.
[127] Zimmerman & Spann (1999) Am Fam Physician 59:113-118, 125-126.
[128] Dreesen (1997) Vaccine 15 Suppl:S2-6.
[129] MMWR Morb Mortal Wkly Rep Jan. 16, 1998;47(1): 12, 19.
[130] Anderson (2000) Vaccine 19 Suppl 1:S59-65.
[131] Kahn (2000) Curr Opin Pediatr 12:257-262.
[132] Crowe (1995) Vaccine 13:415-421.
[133] McMichael (2000) Vaccine 19 Suppl 1:S101-107.
[134] Schuchat (1999) Lancet 353(9146):51-6.
[135] WO02/34771.
[136] Dale (1999) Infect Dis Clin North Am 13:227-43, viii.
[137] Ferretti et al. (2001) PNAS USA 98: 4658-4663.
[138] Kuroda et al. (2001) Lancet 357(9264):1225-1240; see also pages 1218-1219.
[139] J. Toxicol Clin Toxicol (2001) 39:85-100.
[140] Demicheli et al. (1998) Vaccine 16:880-884.
[141] Stepanov et al (1996) J. Biotechnol 44:155-160.
[142] Ingram (2001) Trends Neurosci 24:305-307.
[143] Rosenberg (2001) Nature 411:380-384.
[144] Moingeon (2001) Vaccine 19:1305-1326.
[145] Current Protocols in Molecular Biology (F. M. Ausubel et al., eds., 1987) Supplement 30.
[146] Smith & Waterman (1981) Adv. Appl. Math. 2: 482-489.

SEQUENCE LISTING

```
<160> NUMBER OF SEQ ID NOS: 1

<210> SEQ ID NO 1
<211> LENGTH: 492
<212> TYPE: PRT
<213> ORGANISM: Neisseria meningitidis

<400> SEQUENCE: 1

Met Phe Lys Arg Ser Val Ile Ala Met Ala Cys Ile Phe Ala Leu Ser
 1               5                  10                  15

Ala Cys Gly Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60

Ser Ala Gln Gly Gly Gln Asp Met Ala Ala Val Ser Glu Glu Asn Thr
65                  70                  75                  80

Gly Asn Gly Gly Ala Ala Ala Thr Asp Lys Pro Lys Asn Glu Asp Glu
                85                  90                  95
```

```
Gly Ala Gln Asn Asp Met Pro Gln Asn Ala Ala Asp Thr Asp Ser Leu
            100                 105                 110

Thr Pro Asn His Thr Pro Ala Ser Asn Met Pro Ala Gly Asn Met Glu
        115                 120                 125

Asn Gln Ala Pro Asp Ala Gly Glu Ser Glu Gln Pro Ala Asn Gln Pro
    130                 135                 140

Asp Met Ala Asn Thr Ala Asp Gly Met Gln Gly Asp Asp Pro Ser Ala
145                 150                 155                 160

Gly Gly Glu Asn Ala Gly Asn Thr Ala Ala Gln Gly Thr Asn Gln Ala
                165                 170                 175

Glu Asn Asn Gln Thr Ala Gly Ser Gln Asn Pro Ala Ser Ser Thr Asn
            180                 185                 190

Pro Ser Ala Thr Asn Ser Gly Gly Asp Phe Gly Arg Thr Asn Val Gly
        195                 200                 205

Asn Ser Val Val Ile Asp Gly Pro Ser Gln Asn Ile Thr Leu Thr His
    210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Gly Lys Asn Asp Lys Phe Val
            260                 265                 270

Gly Leu Val Ala Asp Ser Val Gln Met Lys Gly Ile Asn Gln Tyr Ile
        275                 280                 285

Ile Phe Tyr Lys Pro Lys Pro Thr Ser Phe Ala Arg Phe Arg Arg Ser
    290                 295                 300

Ala Arg Ser Arg Arg Ser Leu Pro Ala Glu Met Pro Leu Ile Pro Val
305                 310                 315                 320

Asn Gln Ala Asp Thr Leu Ile Val Asp Gly Glu Ala Val Ser Leu Thr
                325                 330                 335

Gly His Ser Gly Asn Ile Phe Ala Pro Glu Gly Asn Tyr Arg Tyr Leu
            340                 345                 350

Thr Tyr Gly Ala Glu Lys Leu Pro Gly Gly Ser Tyr Ala Leu Arg Val
        355                 360                 365

Gln Gly Glu Pro Ser Lys Gly Glu Met Leu Ala Gly Thr Ala Val Tyr
    370                 375                 380

Asn Gly Glu Val Leu His Phe His Thr Glu Asn Gly Arg Pro Ser Pro
385                 390                 395                 400

Ser Arg Gly Arg Phe Ala Ala Lys Val Asp Phe Gly Ser Lys Ser Val
                405                 410                 415

Asp Gly Ile Ile Asp Ser Gly Asp Gly Leu His Met Gly Thr Gln Lys
            420                 425                 430

Phe Lys Ala Ala Ile Asp Gly Asn Gly Phe Lys Gly Thr Trp Thr Glu
        435                 440                 445

Asn Gly Gly Gly Asp Val Ser Gly Lys Phe Tyr Gly Pro Ala Gly Glu
    450                 455                 460

Glu Val Ala Gly Lys Tyr Ser Tyr Arg Pro Thr Asp Ala Glu Lys Gly
465                 470                 475                 480

Gly Phe Gly Val Phe Ala Gly Lys Lys Glu Gln Asp
                485                 490
```

The invention claimed is:

1. An immunogenic composition comprising (a) an isolated neisserial antigen comprising a ΔG287 form of the wild-type 287protein of strain 394/98 of serogroup B Neisseria meningitidis that retains the immunogenicity of said wild-type 287 protein of said 394/98 of serogroup B Neisseria meningitidis; (b) a CpG oligonucleotide; and (c) biodegradable poly(α-hydroxy acid) microparticles.

2. The composition of claim 1, wherein the neisserial antigen elicits a bactericidal immune response in a recipient mammal against said serogroup B Neisseria meningitidis.

3. The composition of claim 1, wherein the CpG oligonucleotide comprises between about 6 and about 100 deoxyribonucleotides.

4. The composition of claim 1, wherein the microparticles comprise poly(D,L-lactide-co-glycolide).

5. The composition of claim 1, wherein the neisserial antigen is entrapped within the microparticles.

6. The composition of claim 1, wherein the neisserial antigen is adsorbed to the microparticles.

7. The composition of claim 1, wherein the CpG oligonucleotide is entrapped within the microparticles.

8. The composition of claim 1, wherein the CpG oligonucleotide is adsorbed to the microparticles.

9. The composition of claim 2, wherein the microparticles comprise poly(D,L-lactide-co-glycolide).

10. The composition of claim 3, wherein the microparticles comprise poly(D,L-lactide-co-glycolide).

11. The composition of claim 2, wherein the neisserial antigen is entrapped within the microparticles.

12. The composition of claim 3, wherein the neisserial antigen is entrapped within the microparticles.

13. The composition of claim 4, wherein the neisserial antigen is entrapped within the microparticles.

14. The composition of claim 2, wherein the neisserial antigen is adsorbed to the microparticles.

15. The composition of claim 3, wherein the neisserial antigen is adsorbed to the microparticles.

16. The composition of claim 4, wherein the neisserial antigen is adsorbed to the microparticles.

17. The composition of claim 2, wherein the CpG oligonucleotide is entrapped within the microparticles.

18. The composition of claim 3, wherein the CpG oligonucleotide is entrapped within the microparticles.

19. The composition of claim 4, wherein the CpG oligonucleotide is entrapped within the microparticles.

20. The composition of claim 2, wherein the CpG oligonucleotide is adsorbed to the microparticles.

21. The composition of claim 3, wherein the CpG oligonucleotide is adsorbed to the microparticles.

22. The composition of claim 4, wherein the CpG oligonucleotide is adsorbed to the microparticles.

23. The composition of any one of claims 1, 2, 3,4-8, 9, 10, 11, 12, 13, 14, 15, 16, 17, 18, 19, 20, 21 and 22, comprising a further adjuvant.

24. The composition of claim 23, wherein the further adjuvant is MF59 adjuvant.

25. The composition of claim 23, wherein the further adjuvant is an aluminum salt adjuvant.

26. The composition of any one of claims 1, 2, 3 and 4-8, comprising at least one further non-neisserial antigen.

27. The composition of claim 1, wherein said neisserial antigen is a fusion protein comprising said serogroup B Neisseria meningitidis ΔG287 protein.

28. The composition of any one of claims 1, 2, 3, 4-8, 9, 10, 11, 12, 13, 14, 15, 16, 17, 18, 19, 20, 21 and 22, further comprising a pharmaceutically acceptable carrier.

29. The immunogenic composition of claim 6, further comprising an isolated 961c form of the wild-type 961 protein of strain 2996 of serogroup B Neisseria meningitidis that retains the immunogenicity of said wild-type 961 protein of said 2996 of serogroup B Neisseria meningitidis, wherein the antigen is adsorbed to the microparticles.

30. The composition of claim 9, further comprising MF59.

31. The composition of claim 29, further comprising MF59.

32. A method of immunizing a mammal comprising administering to the mammal the composition of any one of claims 1, 2, 3 and 4-8.

*33. The composition of claim 1, further comprising an isolated 919 protein of strain MC58 of serogroup B Neisseria meningitidis.*

*34. The composition of claim 33, further comprising an isolated 961c form of the wild-type 961 protein of strain 2996 of serogroup B Neisseria meningitidis that retains the immunogenicity of said wild-type 961 protein of said 2996 of serogroup B Neisseria meningitidis.*

*35. The composition of claim 34, wherein said composition further comprises an outer-membrane vesicle (OMV) preparation from Neisseria meningitidis.*

*36. The composition of claim 35, wherein the outer-membrane vesicle is obtained from Neisseria meningitidis strain H44/76 or 394/98.*

*37. The immunogenic composition of claim 35 or claim 36, further comprising one or more saccharide antigens from N. meningitidis.*

*38. The immunogenic composition of claim 37, wherein the one or more saccharide antigens are from N. meningitidis serogroup A, C, W135 and/or Y.*

*39. The immunogenic composition of claim 35 or claim 36, comprising a further adjuvant.*

*40. The immunogenic composition of claim 39, wherein the further adjuvant is aluminum salt.*

*41. The immunogenic composition of claim 40, wherein the isolated ΔG287, the isolated 961c, and the isolated 919 proteins are adsorbed to the aluminum salt.*

*42. The immunogenic composition of claim 39, wherein the further adjuvant is aluminum hydroxide gel.*

*43. The immunogenic composition of claim 42, wherein the isolated ΔG287, the isolated 961c, and the isolated 919 proteins are adsorbed to the aluminum hydroxide gel.*

*44. The immunogenic composition of claim 35 or claim 36, wherein the composition is sterile.*

*45. The immunogenic composition of claim 35 or claim 36, wherein the composition is injectable.*

*46. The immunogenic composition of claim 35 or claim 36, wherein the composition is buffered.*

* * * * *